(12) United States Patent
Saito et al.

(10) Patent No.: US 9,404,880 B1
(45) Date of Patent: Aug. 2, 2016

(54) SENSOR AND METHOD OF MANUFACTURING SENSOR

(71) Applicant: KABUSHIKI KAISHA TOSHIBA, Minato-ku, Tokyo (JP)

(72) Inventors: Tatsuro Saito, Yokkaichi Mie (JP); Masayuki Kitamura, Yokkaichi Mie (JP); Atsuko Sakata, Yokkaichi Mie (JP); Akihiro Kajita, Yokkaichi Mie (JP); Atsunobu Isobayashi, Yokkaichi Mie (JP); Tadashi Sakai, Yokohama Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 14/848,267

(22) Filed: Sep. 8, 2015

Related U.S. Application Data

(60) Provisional application No. 62/131,770, filed on Mar. 11, 2015.

(51) Int. Cl.
*H01L 29/16* (2006.01)
*G01N 27/12* (2006.01)

(52) U.S. Cl.
CPC .......... *G01N 27/125* (2013.01); *H01L 29/1606* (2013.01)

(58) Field of Classification Search
CPC ........................... G01N 27/125; H01L 29/1606
See application file for complete search history.

(56) References Cited

U.S. PATENT DOCUMENTS

2015/0376692 A1* 12/2015 Esfandyarpour et al. .................... C12Q 1/6874 506/2

OTHER PUBLICATIONS

Masaki Hasegawa, et al., "Characterization of reduced graphene oxide field-effect transistor and its application to biosensor", Japanese Journal of Applied Physics 53 (2014), pp. 05FD05-1-05FD05-4.
Yasuhide Ohno, et al., "Direct Electrical Detection of DNA Hybridization Based on Electrolyte-Gated Graphene Field-Effect Transistor", Japanese Journal of Applied Physics 52 (2013), pp. 110107-1-110107-4.

* cited by examiner

*Primary Examiner* — Roy Potter
*Assistant Examiner* — Paul Patton
(74) *Attorney, Agent, or Firm* — Holtz, Holtz & Volek PC

(57) ABSTRACT

The sensor includes a first graphene film that is provided on the insulating layer so as to be located in a flow path of a liquid containing the detection target substance, the first graphene film having a first edge that is parallel with a first direction that is along the flow path and a first edge that is parallel with a second direction that is different from the first direction, and the first graphene film having the shape of a band that extends in the second direction. The sensor includes a first electrode that is electrically connected to the first edge of the first graphene film that is parallel with the first direction. The sensor includes a second electrode that is electrically connected to a second edge of the first graphene film that is opposed to the first edge that is parallel with the first direction.

20 Claims, 14 Drawing Sheets

SENSOR AND METHOD OF MANUFACTURING SENSOR

CROSS-REFERENCE TO RELATED APPLICATION

This application is based upon and claims the benefit of U.S. provisional Application No. 62/131,770, filed on Mar. 11, 2015, the entire contents of which are incorporated herein by reference.

FIELD

Embodiments described herein relate generally to a sensor and a method of manufacturing the sensor.

BACKGROUND ART

In recent years, there has been a demand for sensitive materials and structures that can be used to provide biosensors.

In particular, use of the graphene film that substantially changes in electrical characteristics in response to adsorption of or coupling with an atom or molecule on the surface has been studied. A conventional biosensor using the graphene film relies on a change in bulk electron conduction characteristics for detection.

However, the electrical characteristics of the graphene film change in response to adsorption of, or other reactions with, most atoms or molecules, so that it is difficult to locate a detection target substance. To overcome this drawback, the biosensor using the graphene film has to have a surface which only the detection target substance is adsorbed to or coupled with.

Thus, it is difficult for the conventional biosensor to detect a target substance with high sensitivity.

DETAILED DESCRIPTION

A sensor that detects a detection target substance according to an embodiment includes an insulating layer. The sensor includes a first graphene film that is provided on the insulating layer so as to be located in a flow path of a liquid containing the detection target substance, the first graphene film having a first edge that is parallel with a first direction that is along the flow path and a first edge that is parallel with a second direction that is different from the first direction, and the first graphene film having the shape of a band that extends in the second direction. The sensor includes a first electrode that is electrically connected to the first edge of the first graphene film that is parallel with the first direction. The sensor includes a second electrode that is electrically connected to a second edge of the first graphene film that is opposed to the first edge that is parallel with the first direction.

DETAILED DESCRIPTION OF THE INVENTION

As described above, a conventional biosensor using a graphene film relies on a change of bulk electron conduction characteristics for detection. The graphene film exhibits edge state-induced electron conduction characteristics if the graphene film has a line shape as the width of the graphene film decreases.

Figure 1:
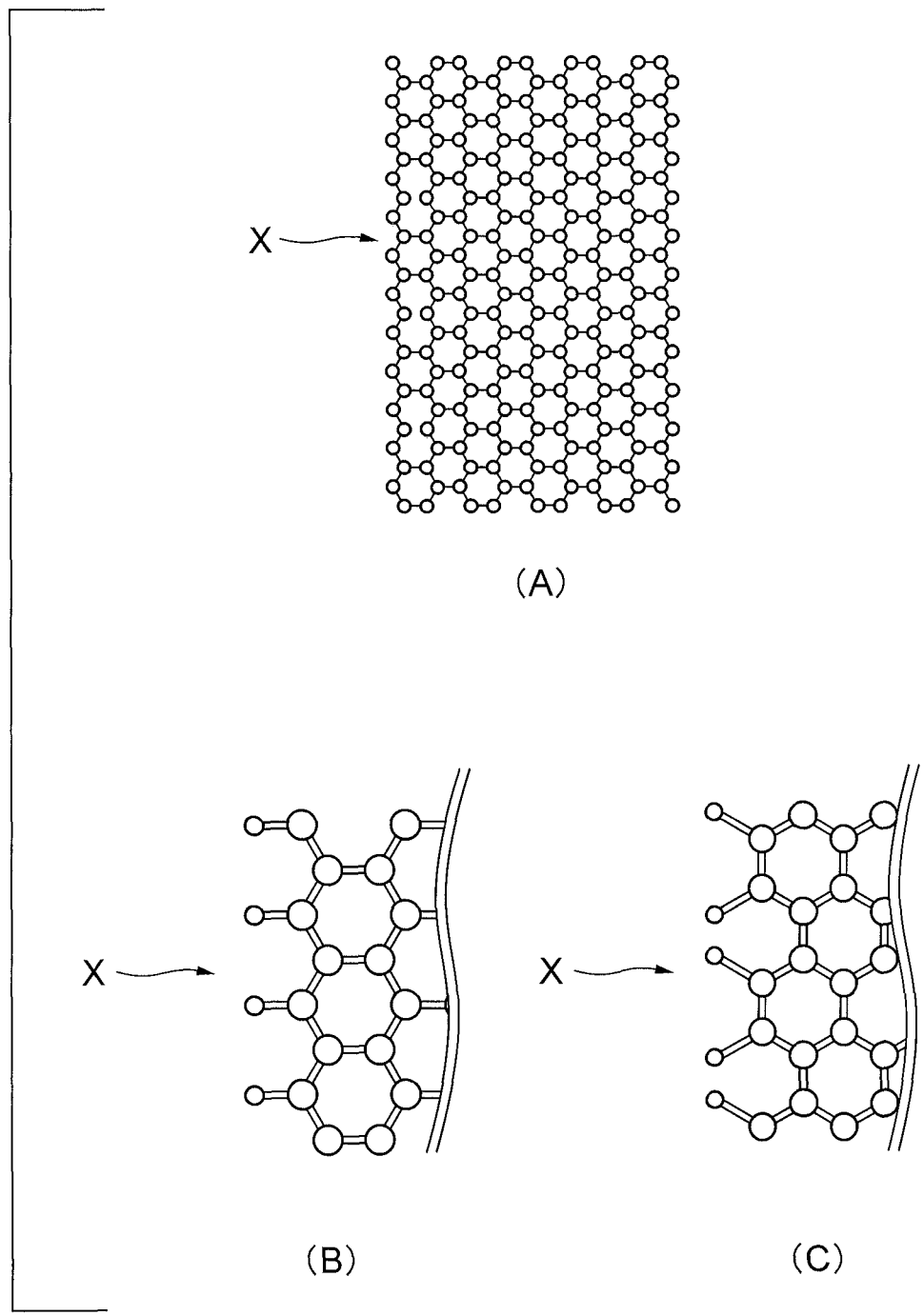
FIG. 1 is a diagram for illustrating a molecular structure of graphene.
Figure 2:
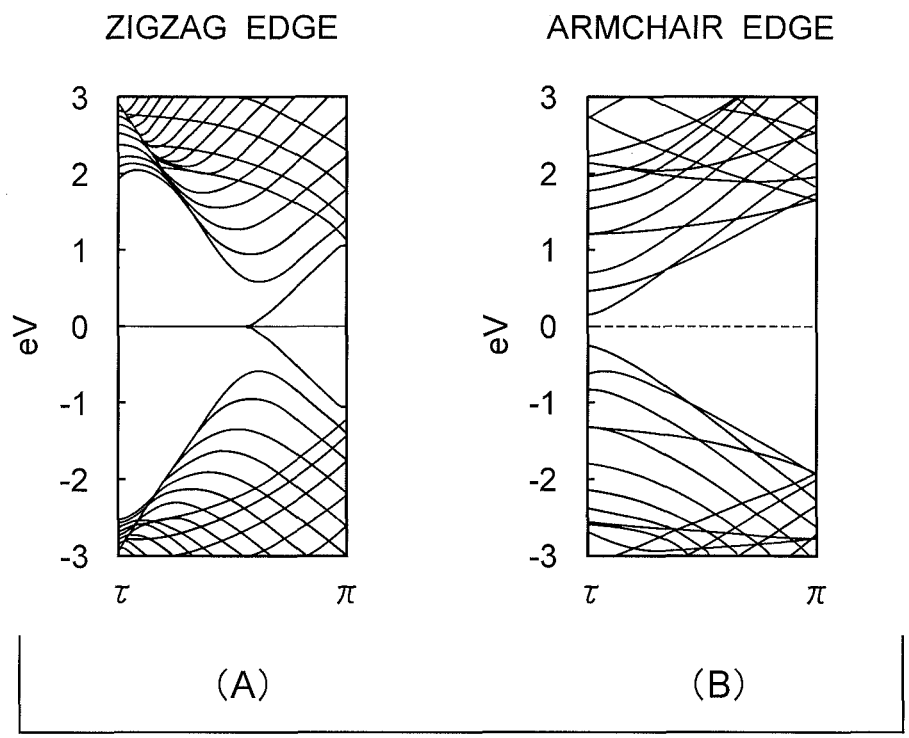
FIG. 2 is a diagram showing the density of states (DOS) of the graphene.

FIG. 1 is a diagram for illustrating a molecular structure of graphene. (A) of FIG. 1 is a diagram showing an example of a molecular structure model of graphene. (B) of FIG. 1 is an enlarged view showing an example (zigzag edge) of a configuration of an edge region "X" of the graphene shown in (A) of FIG. 1. (C) of FIG. 1 is an enlarged view showing another example (armchair edge) of the configuration of the edge region "X" of the graphene shown in (A) of FIG. 1. FIG. 2 is a diagram showing the density of states (DOS) of the graphene. (A) of FIG. 2 is showing an example of the DOS of the zigzag edge of the graphene film. (B) of FIG. 2 is showing an example of the DOS of the armchair edge of the graphene film. In (A) and (B) of FIG. 2, the vertical axis indicates energy (E), and the horizontal axis indicates k-point (an arbitrary point having a symmetry in a reciprocal lattice in the crystal). That is, (A) and (B) of FIG. 2 show energy a carrier can have in a direction (at a k-point) in a crystal.

As shown in FIG. 1, the graphene film has a zigzag edge or an armchair edge. As shown in (A) and (B) of FIG. 2, the zigzag edge and the armchair edge have different DOSs.

Figure 3:
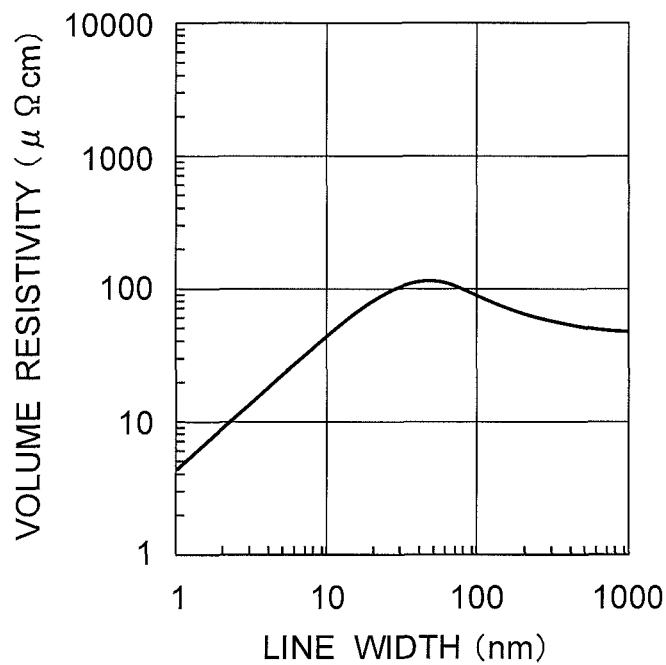
FIG. 3 is a diagram showing an example of a relationship between the width and the volume resistivity of the graphene film.

FIG. 3 is a diagram showing an example of a relationship between the width and the volume resistivity of the graphene film.

As shown in FIG. 3, when the width (line width) of the graphene film becomes equal to or smaller than 100 nm, the edge state-induced characteristics is considered to become remarkable. On the other hand, when the width (line width) of the graphene film becomes equal to or greater than 1 μm, the bulk conduction-induced characteristics is considered to become remarkable.

Figure 4:
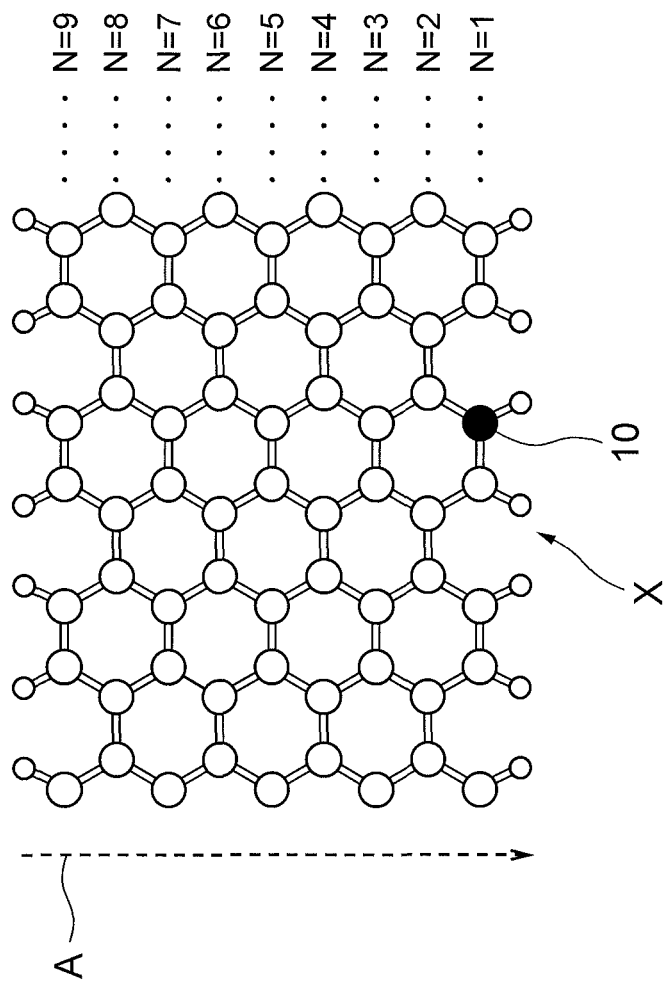
FIG. 4 is a diagram showing an example of a state of a graphene film to which a detection target substance "X" has been adsorbed.

FIG. 4 is a diagram showing an example of a state of a graphene film to which a detection target substance "X" has been adsorbed. The graphene film shown in FIG. 4 has armchair edges at the opposite ends in the first direction "A" of the flow path of the detection target substance. The graphene film has four or three six-membered rings of carbon atoms arranged in the first direction "A" (that is, N (=9) carbon atoms are coupled in the first direction "A"). Furthermore, in the example shown in FIG. 4, the detection target substance is adsorbed to the first (N=1) carbon atom from one edge. The "adsorption" of the detection target substance to the carbon atom used herein also means that the detection target substance comes into contact with the carbon atom, that the detection target substance replaces the carbon atom, or that the detection target substance is in contact with the carbon atom via some other substance.

The resistance of the graphene film having the armchair edge decreases (AGNR), while the resistance of the graphene film having the zigzag edge increases (ZGNR). If the detection target substance is adsorbed to the graphene film having the armchair edge, the resistance and the DOS are considered to change in accordance with the composition of the detection target substance.

The edge state-induced electron conduction characteristics change with the width of the graphene film.

As described above, as the width of the graphene film decreases, the graphene film exhibits edge state-induced electron conduction characteristics. The edge state-induced electron conduction characteristics are sensitively modulated in response to adsorption of or reaction with a foreign matter. Furthermore, the extent of the modulation varies with the width of the graphene film.

Therefore, a plurality of detection target substances can be detected at the same time with high sensitivity by monitoring the extent of the modulation of the edge state-induced electron conduction characteristics of graphene films of different line widths.

Thus, according to embodiments, graphene is used in a detecting part for a detection target substance. In particular, according to the embodiments, biosensors are proposed that use a plurality of graphene films of different small widths and can detect a plurality of detection target substances at the same time or can detect a detection target substance with higher sensitivity.

In the following, embodiments will be described with reference to the drawings.

First Embodiment

First, a configuration of a biosensor according to a first embodiment will be described.

The biosensor according to this embodiment is to detect a detection target substance, such as an ion, an enzyme, a DNA, an antigen or antibody, or a protein. That is, the biosensor serves as an ion sensor, an enzyme sensor, a DNA sensor, an antigen or antibody sensor, or a protein sensor.

Figure 5:
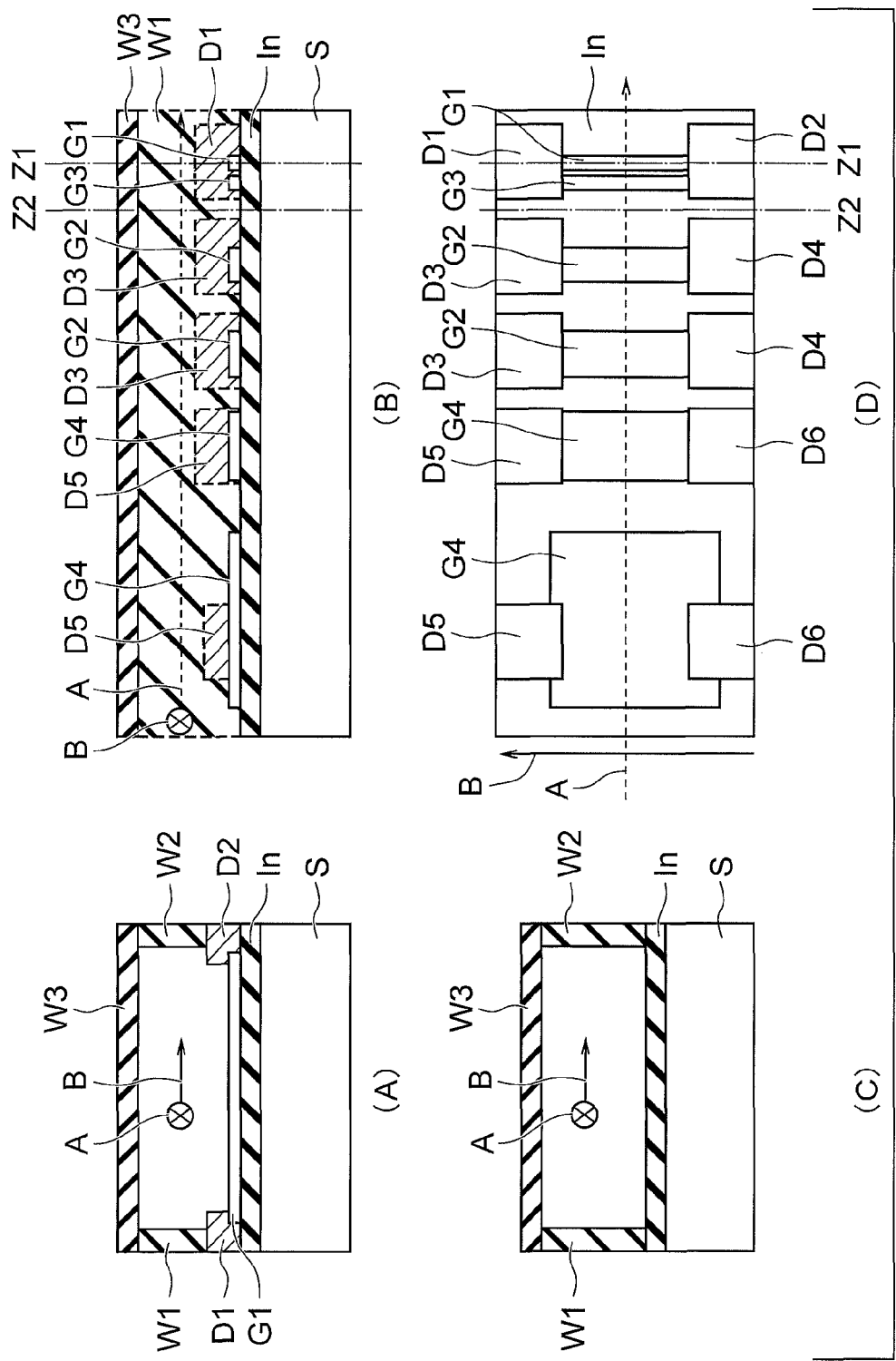
FIG. 5 is a diagram showing a configuration of the biosensor according to the first embodiment.

FIG. 5 is a diagram showing a configuration of the biosensor according to the first embodiment. (A) of FIG. 5 is a cross-sectional view of the biosensor taken along a plane "Z1" perpendicular to a first direction "A" of a flow path of a detection target substance of the biosensor. (B) of FIG. 5 is a cross-sectional view of the biosensor taken along the first direction "A" of the flow path of the detection target substance of the biosensor. (C) of FIG. 5 is a cross-sectional view of the biosensor taken along a plane "Z2" perpendicular to the first direction "A" of the flow path of the detection target substance of the biosensor. (D) of FIG. 5 is a top view of the biosensor. In (D) of FIG. 5, illustration of a first side wall insulating layer "W1", a second side wall insulating layer "W2" and an upper insulating layer "W3" is omitted.

As shown in FIG. 5, the biosensor includes a substrate "S", an insulating layer "In", a first graphene film "G1", a second graphene film "G2", a third graphene film "G3", a fourth graphene film "G4", a first electrode "D1", a second electrode "D2", a third electrode "D3", a fourth electrode "D4", a fifth electrode "D5", a sixth electrode "D6", the first side wall insulating layer "W1", the second side wall insulating layer "W2", and the upper insulating layer "W3", for example.

The substrate "S" is a silicon substrate, for example. The substrate "S" may be made of a silicon oxide or a polymer material. The flow path through which the detection target substance to be detected by the biosensor or a medium containing the detection target substance flows is located on the substrate "S".

The insulating layer "In" is provided on the substrate "S". The insulating layer "In" is a silicon oxide film. The insulating layer "In" is intended to prevent discharge. The insulating layer "In" may be incorporated in the substrate "S".

The first graphene film "G1" is provided on the insulating layer "In" so as to be located in the flow path of the detection target substance (liquid (medium) containing the detection target substance). The first graphene film "G1" has an edge that is parallel with the first direction "A", an edge opposed to the edge that is parallel with the first direction "A", an edge that is parallel with a second direction "B", and an edge opposed to the edge that is parallel with the second direction "B". For example, the edge that is parallel with the first direction "A" and the edge opposed thereto are parallel with each other, and the edge that is parallel with the second direction "B" and the edge opposed thereto are parallel with each other. That is, the first graphene film "G1" has a substantially rectangular shape that has edges that are parallel with the first direction "A" and edges that are parallel with the second direction "B", the shape being a band-like shape that extends in the second direction "B", which is different from the first direction "A" that is along the flow path. The first direction "A" and the second direction "B" are perpendicular to each other in a plane parallel with an upper surface of the substrate "S". In the example shown in FIG. 5, the direction of the flow of the detection target substance corresponds to the direction of the arrow of the first direction "A" along the flow path.

The length of the edge of the first graphene film "G1" that is parallel with the first direction "A", that is, the width in the first direction "A", is equal to or smaller than a first prescribed value (100 nm in this example) previously set. The first graphene film "G1" contains at least one six-membered ring of carbon atoms in the first direction "A".

That is, the bulk conduction-induced characteristics of the first graphene film "G1" is reduced, and the first graphene film "G1" exhibits edge state-induced electron conduction characteristics.

The third graphene film "G3" is provided on the insulating layer "In" so as to be located in the flow path. The third graphene film "G3" has an edge that is parallel with the first direction "A", an edge opposed to the edge that is parallel with the first direction "A", an edge that is parallel with the second direction "B", and an edge opposed to the edge that is parallel with the second direction "B". For example, the edge that is parallel with the first direction "A" and the edge opposed thereto are parallel with each other, and the edge that is parallel with the second direction "B" and the edge opposed thereto are parallel with each other. That is, the third graphene film "G3" has a substantially rectangular shape that has edges that are parallel with the first direction "A" and edges that are parallel with the second direction "B", for example, the shape being a band-like shape that extends in the second direction "B".

The length of the edge of the third graphene film "G3" that is parallel with the first direction "A", that is, the width in the first direction "A", is equal to or smaller than the first prescribed value. In the example shown in FIG. 5, the width of the third graphene layer "G3" in the first direction "A" is set to be equal to the width of the first graphene layer "G1." in the first direction "A". The third graphene film "G3" contains at least one six-membered ring of carbon atoms in the first direction "A".

That is, the bulk conduction-induced characteristics of the third graphene film "G3" is reduced, and the third graphene film "G3" exhibits edge state-induced electron conduction characteristics.

The first electrode "D1." is electrically connected to the edge of the first graphene film "G1." that is parallel with the first direction "A". Furthermore, the first electrode "D1" is electrically connected to the edge of the third graphene film "G3" that is parallel with the first direction "A". In the example shown in FIG. 5, the first electrode "D1" is provided on the insulating layer "In" and the edges of the first and third graphene films "G1" and "G3" that are parallel with the first direction "A".

The second electrode "D2" is electrically connected to the edge of the first graphene film "G1" that is opposed to the edge that is parallel with the first direction "A". Furthermore, the second electrode "D2" is electrically connected to the edge of the third graphene film "G3" that is opposed to the edge that is parallel with the first direction "A". In the example shown in FIG. 5, the second electrode "D2" is provided on the insulating layer "In" and the edges of the first and third graphene films "G1" and "G3" that are opposed to the edges that are parallel with the first direction "A".

As described above, the first and third graphene films "G1" and "G3" are electrically connected in parallel with each other between the first electrode "D1" and the second electrode "D2". In other words, the first and second electrodes "D1" and "D2" transmit signals for the first and third graphene films "G1" and "G3".

The edges of the first and third graphene films "G1" and "G3" that are parallel with the second direction "B" are zigzag edges or armchair edges.

The second graphene film "G2" is provided on the insulating layer "In" so as to be located in the flow path. The second graphene film "G2" has an edge that is parallel with the first direction "A", an edge opposed to the edge that is parallel with the first direction "A", an edge that is parallel with the second direction "B", and an edge opposed to the edge that is parallel with the second direction "B". For example, the edge that is parallel with the first direction "A" and the edge opposed thereto are parallel with each other, and the edge that is parallel with the second direction "B" and the edge opposed thereto are parallel with each other. That is, the second graphene film "G2" has a substantially rectangular shape that has edges that are parallel with the first direction "A" and edges that are parallel with the second direction "B", for example, the shape being a band-like shape that extends in the second direction "B".

The third electrode "D3" is electrically connected to the edge of the second graphene film "G2" that is parallel with the first direction "A". In the example shown in FIG. 5, the third electrode "D3" is provided on the insulating layer "In" and the edge of the second graphene film "G2" that is parallel with the first direction "A".

The fourth electrode "D4" is electrically connected to the edge of the second graphene film "G2" that is opposed to the edge that is parallel with the first direction "A". In the example shown in FIG. 5, the fourth electrode "D4" is provided on the insulating layer "In" and the edge of the second graphene film "G2" that is opposed to the edge that is parallel with the first direction "A".

As described above, the second graphene film "G2" is electrically connected between the third electrode "D3" and the fourth electrode "D4". In other words, the third and fourth electrodes "D3" and "D4" transmit a signal for the second graphene film "G2".

The length of the edge of the second graphene film "G2" that is parallel with the first direction "A", that is, the width in the first direction "A", is equal to or smaller than the first prescribed value. That is, the bulk conduction-induced characteristics of the second graphene film "G2" is reduced, and the second graphene film "G2" exhibits edge state-induced electron conduction characteristics.

The width of the second graphene film "G2" differs from the width of the first graphene film "G1." in the first direction "A". In the example shown in FIG. 5, the width of the second graphene film "G2" in the first direction "A" is equal to or smaller than the first prescribed value and is greater than the width of the first graphene film "G1" in the first direction "A". The second graphene film "G2" contains at least one six-membered ring of carbon atoms in the first direction "A".

Thus, the second graphene film "G2" exhibits edge state-induced electron conduction characteristics that differ from those of the first and third graphene films "G1." and "G3".

The fourth graphene film "G4" is provided on the insulating layer "In" so as to be located in the flow path. The fourth graphene film "G4" has an edge that is parallel with the first direction "A", an edge opposed to the edge that is parallel with the first direction "A", an edge that is parallel with the second direction "B", and an edge opposed to the edge that is parallel with the second direction "B". For example, the edge that is parallel with the first direction "A" and the edge opposed thereto are parallel with each other, and the edge that is parallel with the second direction "B" and the edge opposed thereto are parallel with each other. That is, the fourth graphene film "G4" has a substantially rectangular shape that has edges that are parallel with the first direction "A" and edges that are parallel with the second direction "B", for example, the shape being a band-like shape that extends in the second direction "B".

The length of the edge of the fourth graphene film "G4" that is parallel with the first direction "A", that is, the width in the first direction "A", is equal to or greater than a second prescribed value (1 μm, for example) that is greater than the first prescribed value (100 nm) previously set.

As a result, the fourth graphene film "G4" exhibits bulk conduction-induced characteristics.

The fifth electrode "D5" is electrically connected to the edge of the fourth graphene film "G4" that is parallel with the first direction "A". In the example shown in FIG. 5, the fifth electrode "D5" is provided on the insulating layer "In" and the edge of the fourth graphene film "G4" that is parallel with the first direction "A".

The sixth electrode "D6" is electrically connected to the edge of the fourth graphene film "G4" that is opposed to the edge that is parallel with the first direction "A". In the example shown in FIG. 5, the sixth electrode "D6" is provided on the insulating layer "In" and the edge of the fourth graphene film "G4" that is opposed to the edge that is parallel with the first direction "A".

As described above, the fourth graphene film "G4" is electrically connected between the fifth electrode "D5" and the sixth electrode "D6". In other words, the fifth and sixth electrodes "D5" and "D6" transmit a signal for the fourth graphene film "G4".

The edges of the first to fourth graphene films "G1" to "G4" that are parallel with the second direction "B" are zigzag edges or armchair edges.

Although the first to fourth graphene films "G1" to "G4" have been described as having a substantially rectangular shape as an example, the first to fourth graphene films "G1" to "G4" may have the shape of a parallelogram or trapezoid, for example.

The first to sixth electrodes "D1" to "D6" contains any of Al, Cu, W and Ni.

A catalyst (not shown), a backing film (not shown) or the like for formation of the graphene films may be provided between the first to fourth graphene films "G1" to "G4" and the insulating layer "In".

The first side wall insulating layer "W1" is provided on the insulating layer "In" along the first direction "A" on the right side of the flow path. The second side wall insulating layer "W2" is provided on the insulating layer "In" along the first direction "A" on the left side of the flow path. The upper insulating layer "W3" is provided above the flow path along the first direction "A" and is connected to upper parts of the first and second side wall insulating layers "W1" and "W2".

The first side wall insulating layer "W1", the second side wall insulating layer "W2" and the upper insulating layer "W3" are made of an insulating material, such as $SiO_2$, SiN or a polymer material. The first side wall insulating layer "W1", the second side wall insulating layer "W2" and the upper insulating layer "W3" may be integrally formed.

Suppose that a detection target substance is flowed into the flow path of the biosensor in the first direction "A", for example. Then, the detection target substance is adsorbed to a carbon atom of each of the first to fourth graphene films "G1" to "G4". As described above, the "adsorption" of the detection target substance to the carbon atom also means that the detection target substance comes into contact with the carbon atom, that the detection target substance replaces the carbon atom, or that the detection target substance is in contact with the carbon atom via some other substance.

The resistances between the first electrode "D1" and the second electrode "D2", between the third electrode "D3" and the fourth electrode "D4" and between the fifth electrode "D5" and the sixth electrode "D6" are measured. The composition of the detection target substance can be determined from the resistances, the characteristics shown in FIG. 8 and the like. The detection of the detection target substance can rely on the extent to which an electrical characteristic (resistance, for example) increases or decreases. However, the detection of the detection target substance does not have to rely only on the extent to which an electrical characteristic increases or decreases.

For example, graphene films of line widths smaller than the size of the detection target substance can be formed with a high density over a wide area by using a semiconductor manufacturing technique. In that case, if each graphene film is connected to a separate electrode and individually monitored, the size of the detection target substance can be measured.

That is, the biosensor according to this embodiment can also individually evaluate more detection target substances, including determining the relative amounts of the detection target substances.

Next, an example of a method of manufacturing the biosensor configured as described above will be described. FIGS. 6 to 11 are diagrams examples of steps of the method of manufacturing the biosensor according to the first embodiment. (A) of FIGS. 6 to 11 are cross-sectional views taken along the plane "Z1" perpendicular to the first direction "A" of the flow path of the detection target substance. (B) of FIGS. 6 to 11 are cross-sectional views taken along the first direction "A" of the flow path of the detection target substance.

Figure 6:
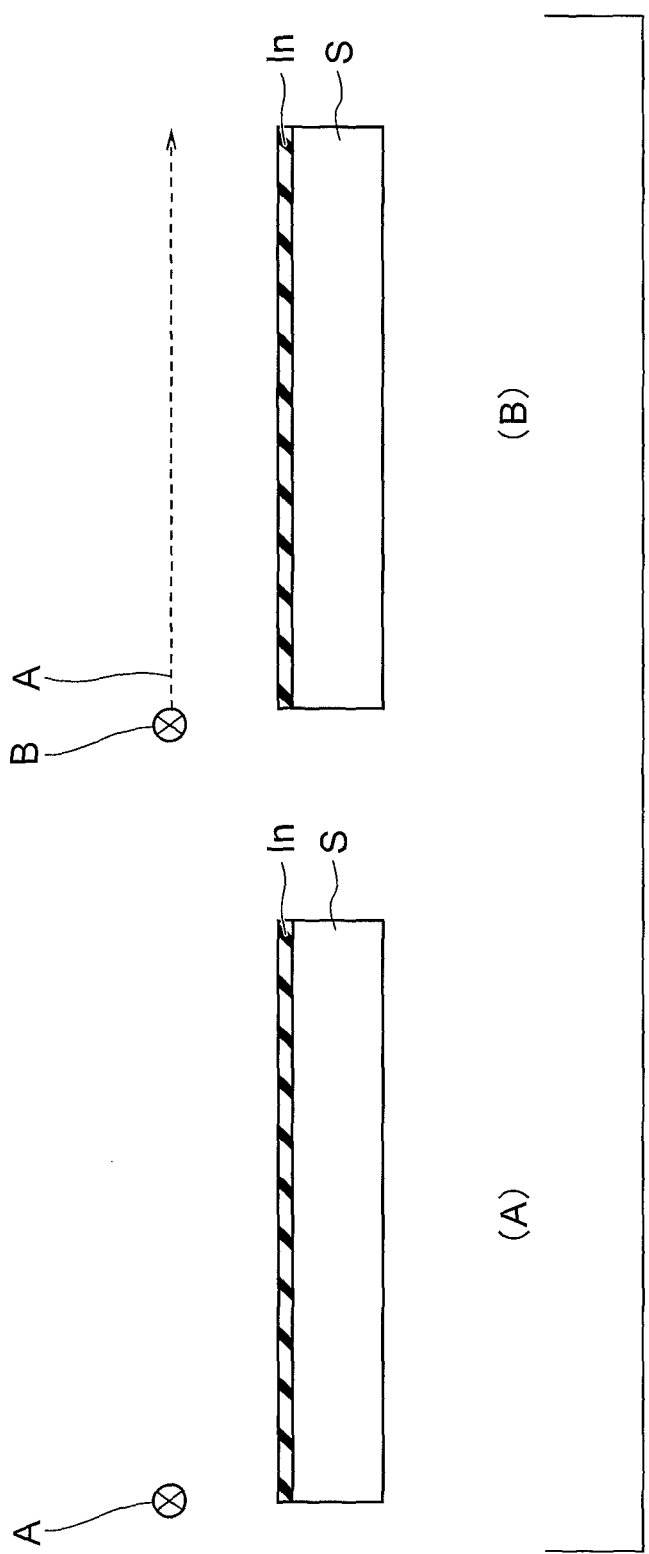
FIG. 6 is a diagram showing an example of step of the method of manufacturing the biosensor according to the first embodiment.

First, as shown in FIG. 6, the insulating layer "In" is formed on the substrate "S".

Figure 7:
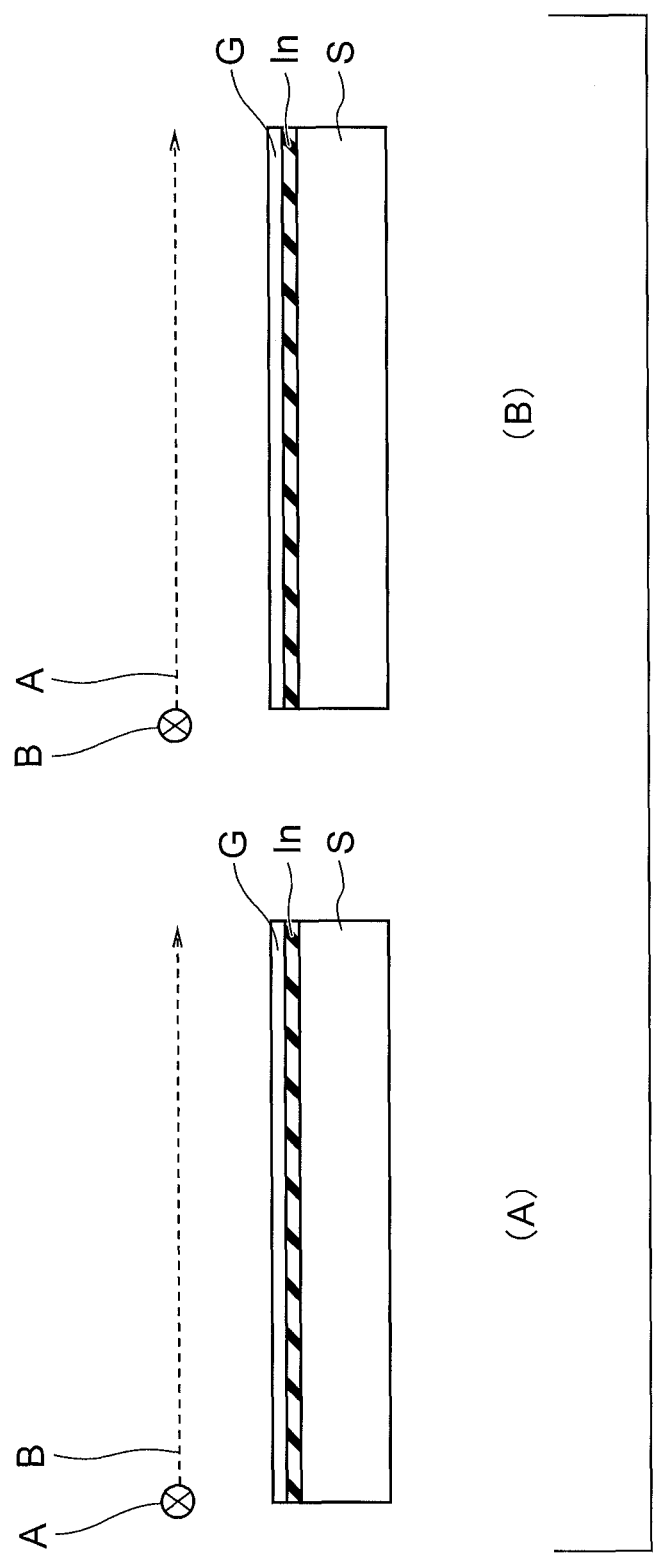
FIG. 7 is a diagram showing an example of step of the method of manufacturing the biosensor according to the first embodiment, and continuous from FIG. 6.

As shown in FIG. 7, a graphene film "G" is then formed on the insulating layer "In" by chemical vapor deposition (CVD), for example.

The graphene film "G" may be formed by graphite transfer. When the graphite transfer process is used, graphene patterned by a printing technique may be applied, for example.

Figure 8:
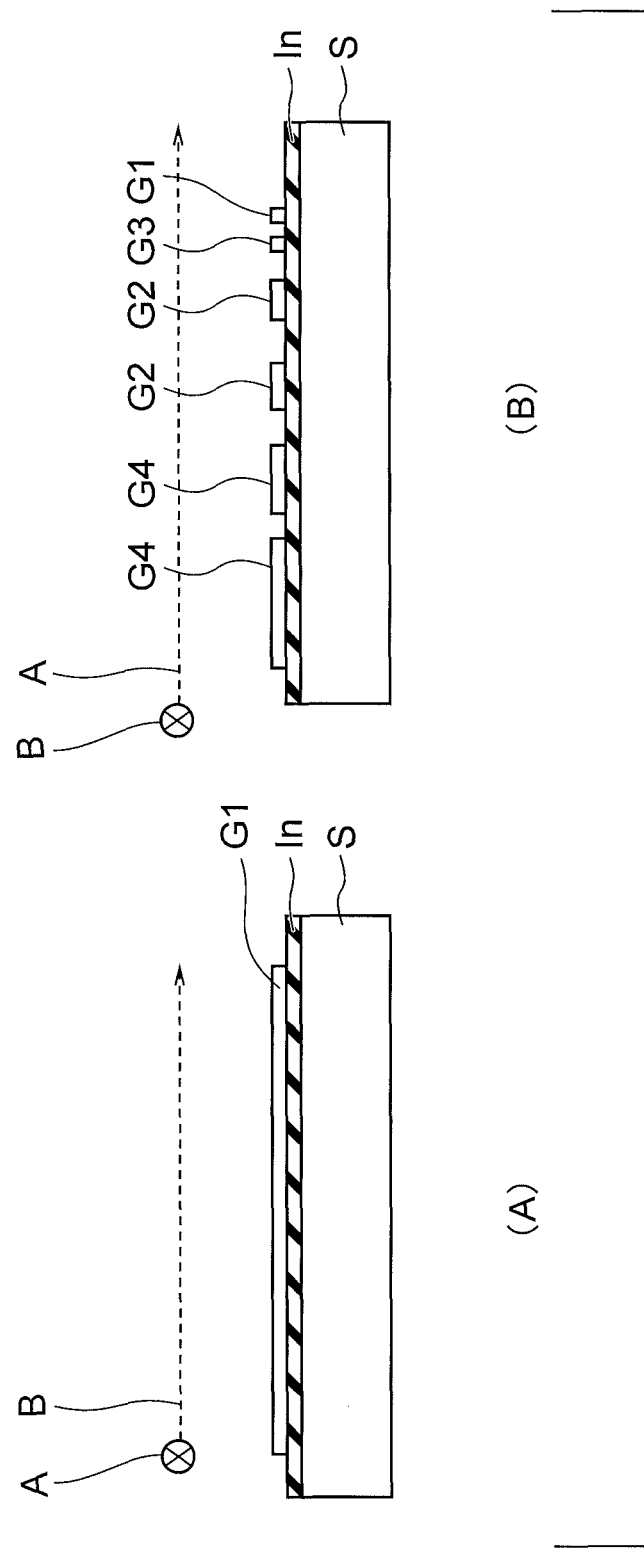
FIG. 8 is a diagram showing an example of step of the method of manufacturing the biosensor according to the first embodiment, and continuous from FIG. 7.

As shown in FIG. 8, the graphene film "G" is patterned by lithography, for example. In this step, in the case where only changes in edge state-induced characteristics are to be monitored, a hard mask used in the patterning (not shown) or the like may be left on the graphene film.

In this way, the first to fourth graphene films "G1" to "G4" having the shape of a band that extends in the second direction "B" are formed on the insulating layer "In" so as to be located in the flow path.

As an alternative, a backing material (not shown) for formation of the graphene film may be patterned in advance, and the first to fourth graphene films "G1" to "G4" may then be selectively formed by CVD or the like.

In this way, the first to third graphene films "G1" to "G3" that have a width in the first direction "A" that is equal to or smaller than the first prescribed value (100 nm, in this example), for which an edge state-induced electron state is dominant, and the fourth graphene film "G4" that has a width in the first direction "A" that is equal to or greater than the second prescribed value (1 for example), which exhibits bulk electron conduction characteristics, are formed.

Figure 9:
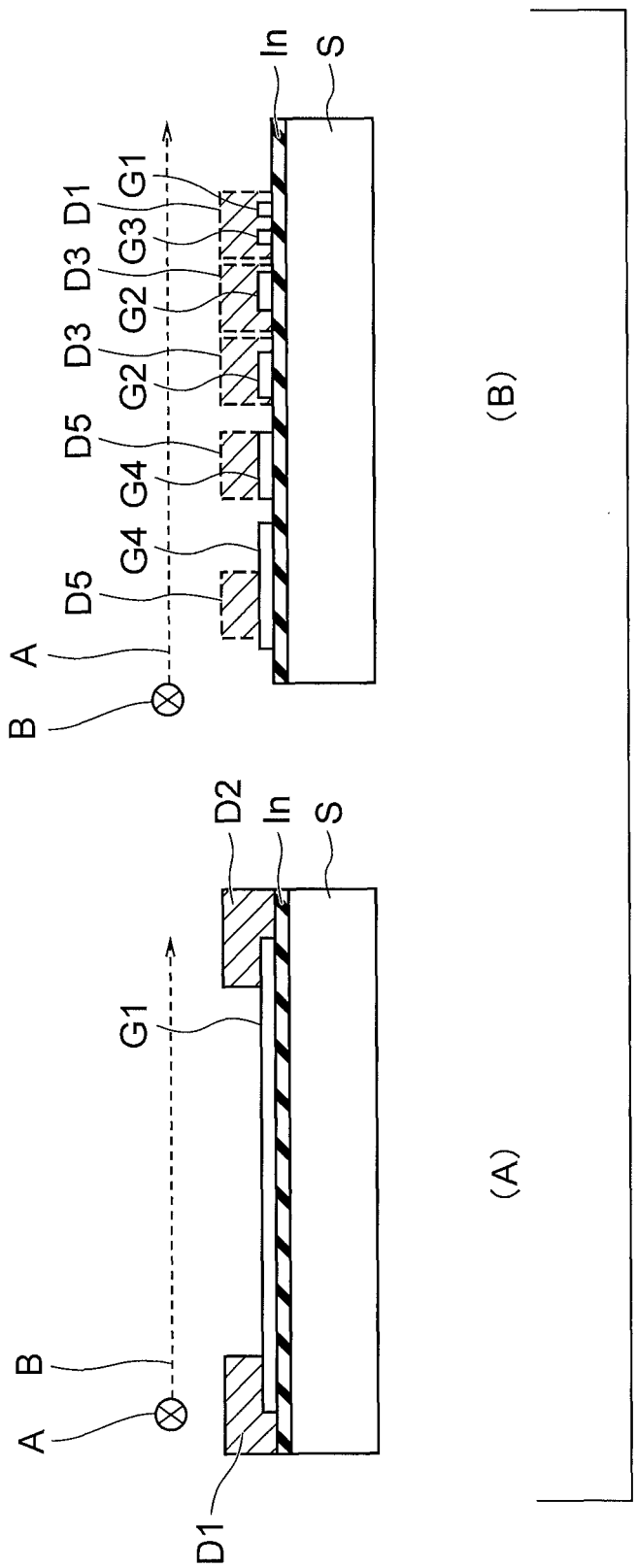
FIG. 9 is a diagram showing an example of step of the method of manufacturing the biosensor according to the first embodiment, and continuous from FIG. 8.

As shown in FIG. 9, the first, third and fifth electrodes "D1", "D3" and "D5" electrically connected to the edges of the first to fourth graphene films "G1" to "G4" that are parallel with the first direction "A" and the second, fourth and sixth electrodes "D2", "D4" and "D6" electrically connected to the edges of the first to fourth graphene films "G1" to "G4" that are opposed to the edges that are parallel with the first direction "A" are formed.

As described above, the first to sixth electrodes "D1" to "D6" are made of a material containing any of Al, Cu, W and Ni.

An insulating layer of $SiO_2$ or the like is deposited on a substrate (not shown) that can be lifted off, the insulating layer is patterned, and the patterned insulating layer is lifted off, for example. In this way, as shown in FIG. 10, the first side wall insulating layer "W1", the second side wall insulating layer "W2", and the upper insulating layer "W3" connected to the upper parts of the first and second side wall insulating layers "W1" and "W2" are formed.

Figure 10:
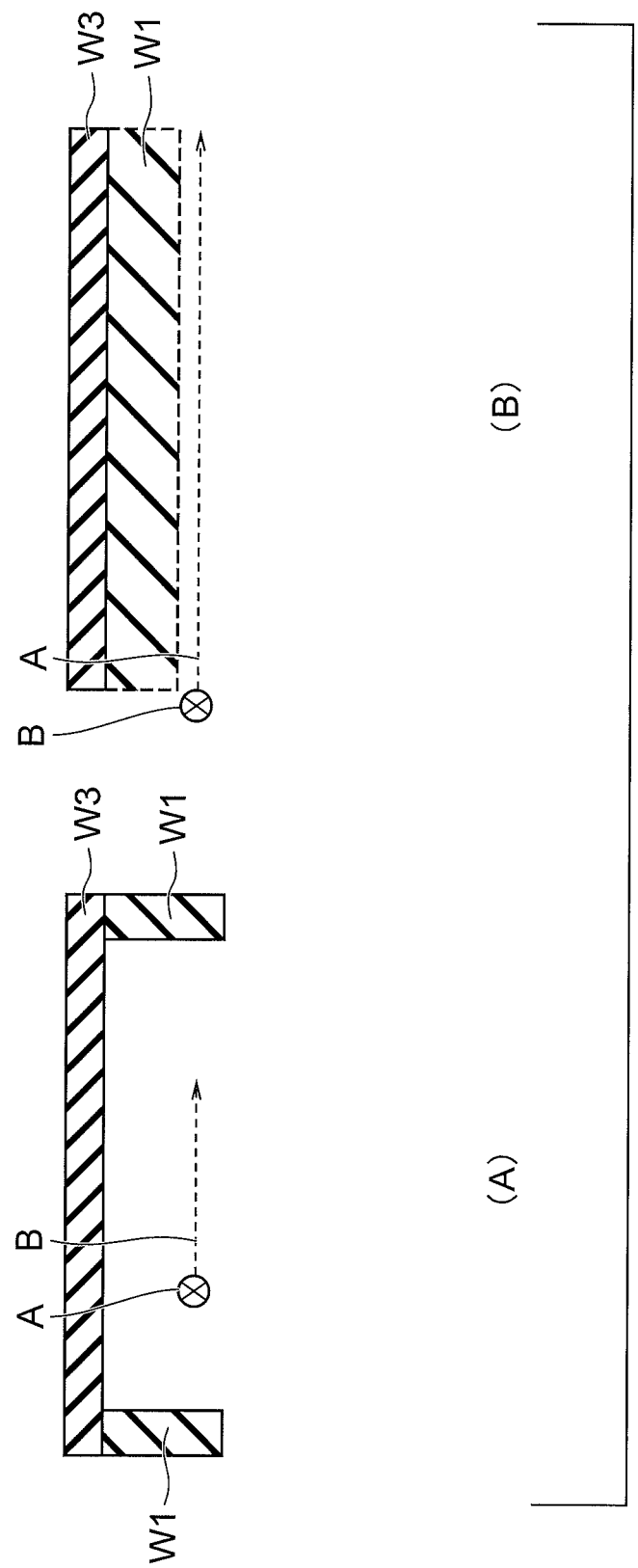
FIG. 10 is a diagram showing an example of step of the method of manufacturing the biosensor according to the first embodiment, and continuous from FIG. 9.
Figure 11:
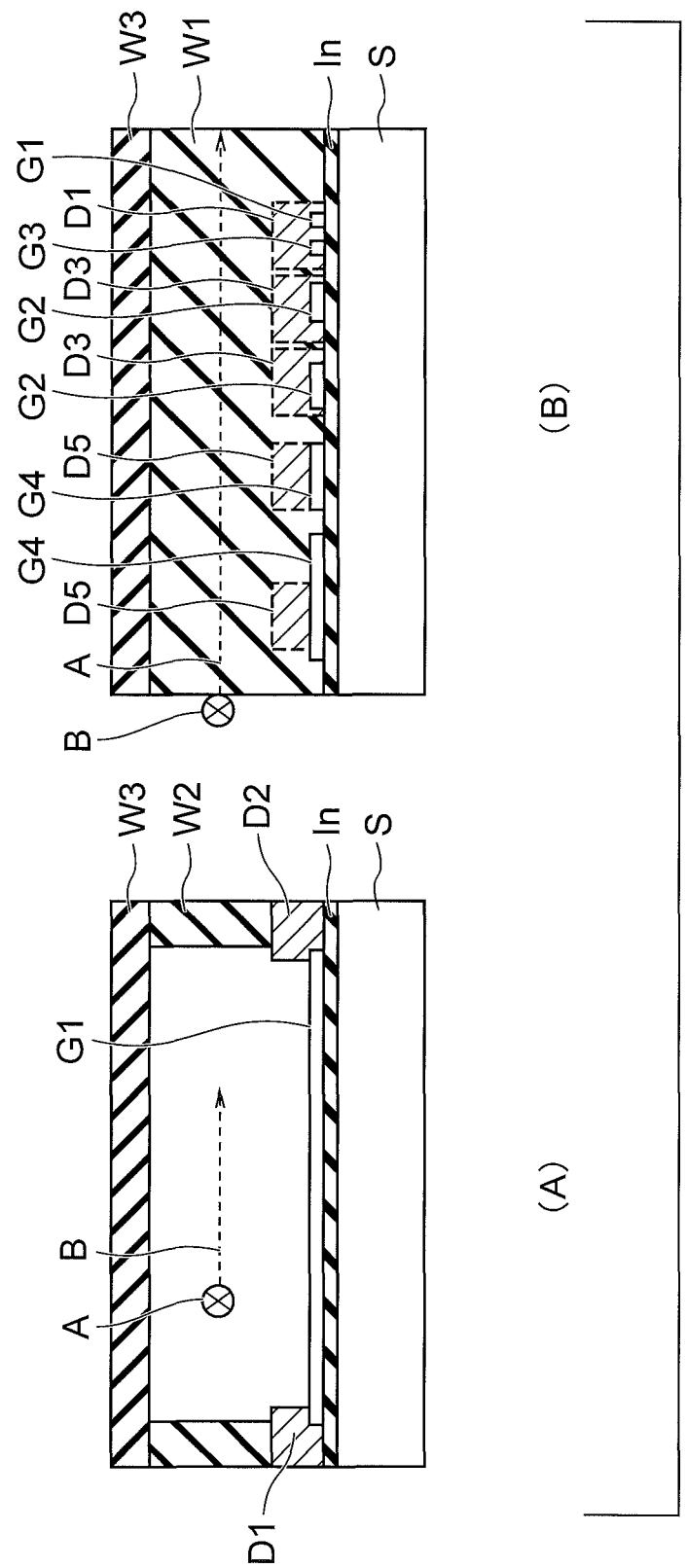
FIG. 11 is a diagram showing an example of step of the method of manufacturing the biosensor according to the first embodiment, and continuous from FIG. 10.

As shown in FIG. 11, the substrate "S" with the first to fourth graphene films "G1" to "G4" formed thereon as shown in FIG. 9 and the structure of the first side wall insulating layer "W1", the second side wall insulating layer "W2" and the upper insulating layer "W3" formed in the step shown in FIG. 10 is then bonded to each other so as to form the flow path.

In this way, the first side wall insulating layer "W1" extending in the first direction "A" on the right side of the flow path on the insulating layer "In", the second side wall insulating layer "W2" extending in the first direction "A" on the left side of the flow path on the insulating layer "In", and the upper insulating layer "W3" connected to the upper parts of the first and second side wall insulating layers "W1" and "W2" and extending in the first direction "A" above the flow path are formed.

In the process described above, the biosensor shown in FIG. 5 is completed.

As described above, the biosensor according to this embodiment can detect a detection target substance with high sensitivity.

Second Embodiment

A second embodiment described below concerns another example of the method of manufacturing the biosensor.

Figure 12:
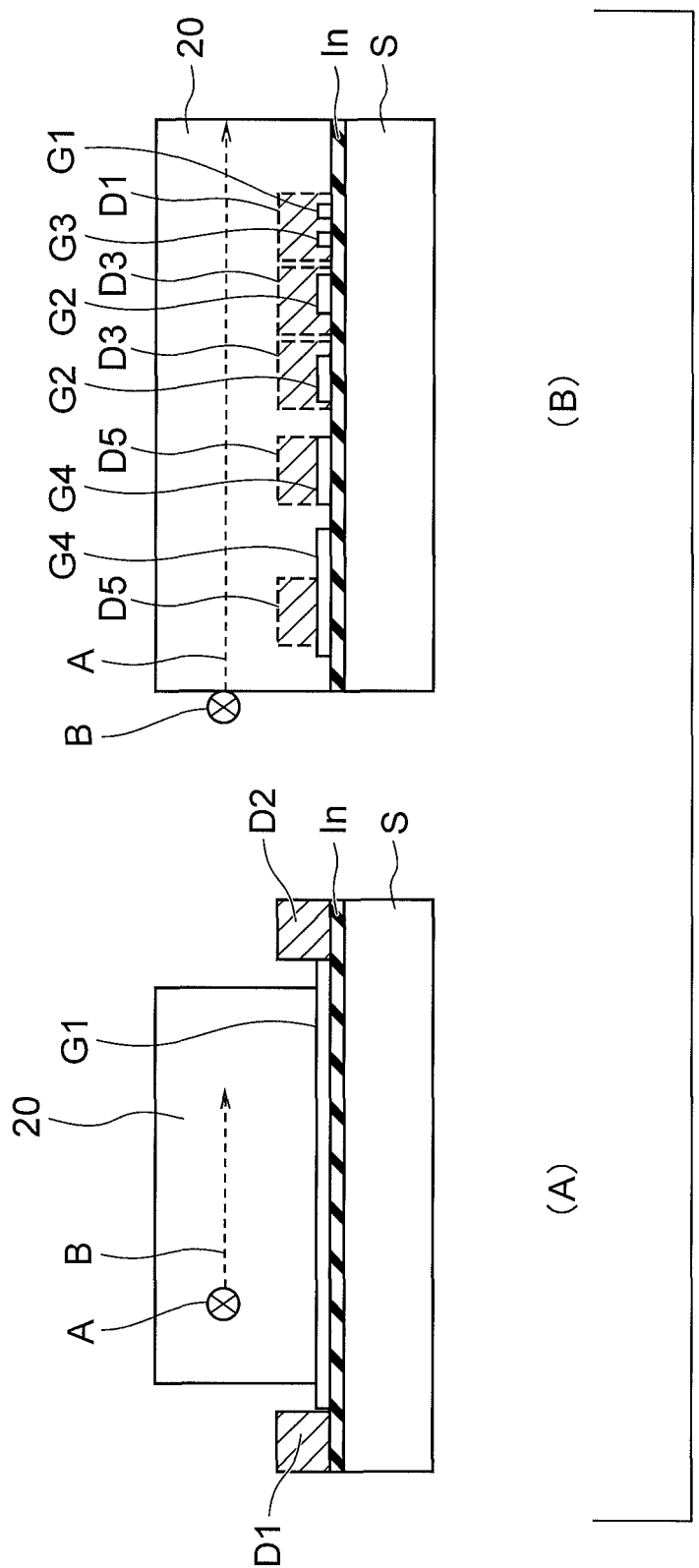
FIG. 12 is a diagram showing an example of step of a method of manufacturing the biosensor according to the second embodiment, and continuous from FIG. 8.
Figure 13:
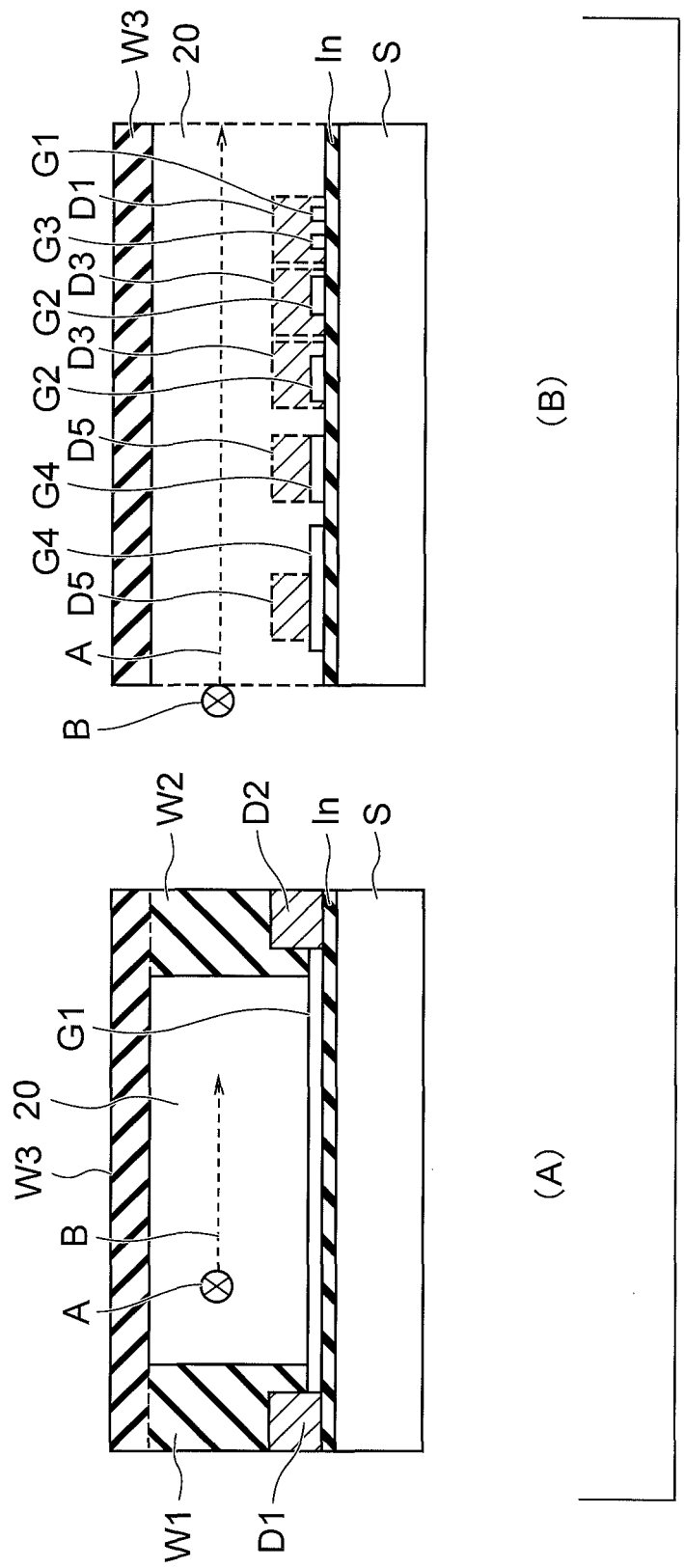
FIG. 13 is a diagram showing an example of step of a method of manufacturing the biosensor according to the second embodiment, and continuous from FIG. 12.
Figure 14:
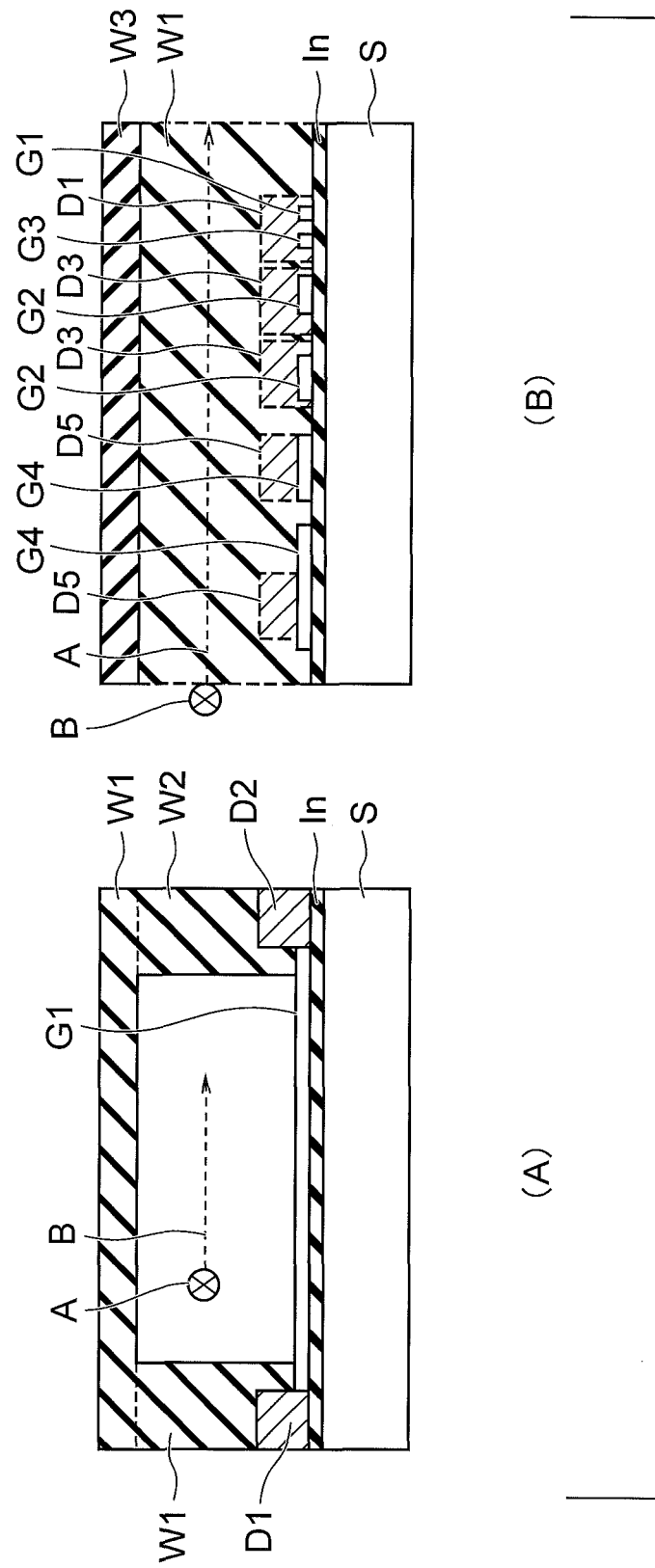
FIG. 14 is a diagram showing an example of step of a method of manufacturing the biosensor according to the second embodiment, and continuous from FIG. 13.

FIGS. 12 to 14 are diagrams showing examples of steps of a method of manufacturing the biosensor according to the second embodiment. (A) of FIG. 12 to (A) FIG. 14 are cross-sectional views taken along the plane "Z1" perpendicular to the first direction "A" of the flow path of the detection target substance. (B) of FIG. 12 to (B) of FIG. 14 are cross-sectional views taken along the first direction "A" of the flow path of the detection target substance. The method of manufacturing the biosensor according to the second embodiment is the same as the method according to the first embodiment until the step shown in FIG. 9.

As described above with regard to the first embodiment, the first, third and fifth electrodes "D1", "D3" and "D5" electrically connected to the edges of the first to fourth graphene films "G1" to "G4" that are parallel with the first direction "A" and the second, fourth and sixth electrodes "D2", "D4" and "D6" electrically connected to the edges of the first to fourth graphene films "G1" to "G4" that are opposed to the edges that are parallel with the first direction "A" are formed (FIG. 9).

As shown in FIG. 12, a sacrificial layer 20 of SiN or the like is then formed on the insulating layer "In" and the first to fourth graphene films "G1" to "G4" at a position where the flow path is to be formed.

As shown in FIG. 13, an insulating layer of a material such as $SiO_2$ is then formed on the substrate "S", thereby forming the first side wall insulating layer "W1" extending in the first direction "A" on the right side of the flow path on the insulating layer "In", the second side wall insulating layer "W2" extending in the first direction "A" on the left side of the flow path on the insulating layer "In", and the upper insulating layer "W3" connected to the upper parts of the first and second side wall insulating layers "W1" and "W2" and extending in the first direction "A" above the flow path.

As shown in FIG. 14, the sacrificial layer 20 is selectively removed by wet etching using an etchant such as phosphoric acid, thereby forming the flow path.

In the process described above, the biosensor according to the second embodiment is completed.

In other respects, the configuration of the biosensor formed in the manufacturing method and the method of manufacturing the biosensor are the same as those according to the first embodiment.

The remainder of the characteristics of the operation of the biosensor is the same as that in the first embodiment.

As described above, the biosensor according to this embodiment can detect a detection target substance with high sensitivity.

Third Embodiment

If the width of the graphene film is not sufficiently small, the bulk conduction-induced characteristics can be detected along with the edge state-induced characteristics in detection of the detection target substance. To reduce the bulk conduction-induced characteristics, a protective film can be formed on the graphene film in such a manner that edges of the graphene film are exposed. Such a structure will now be described.

Figure 15:
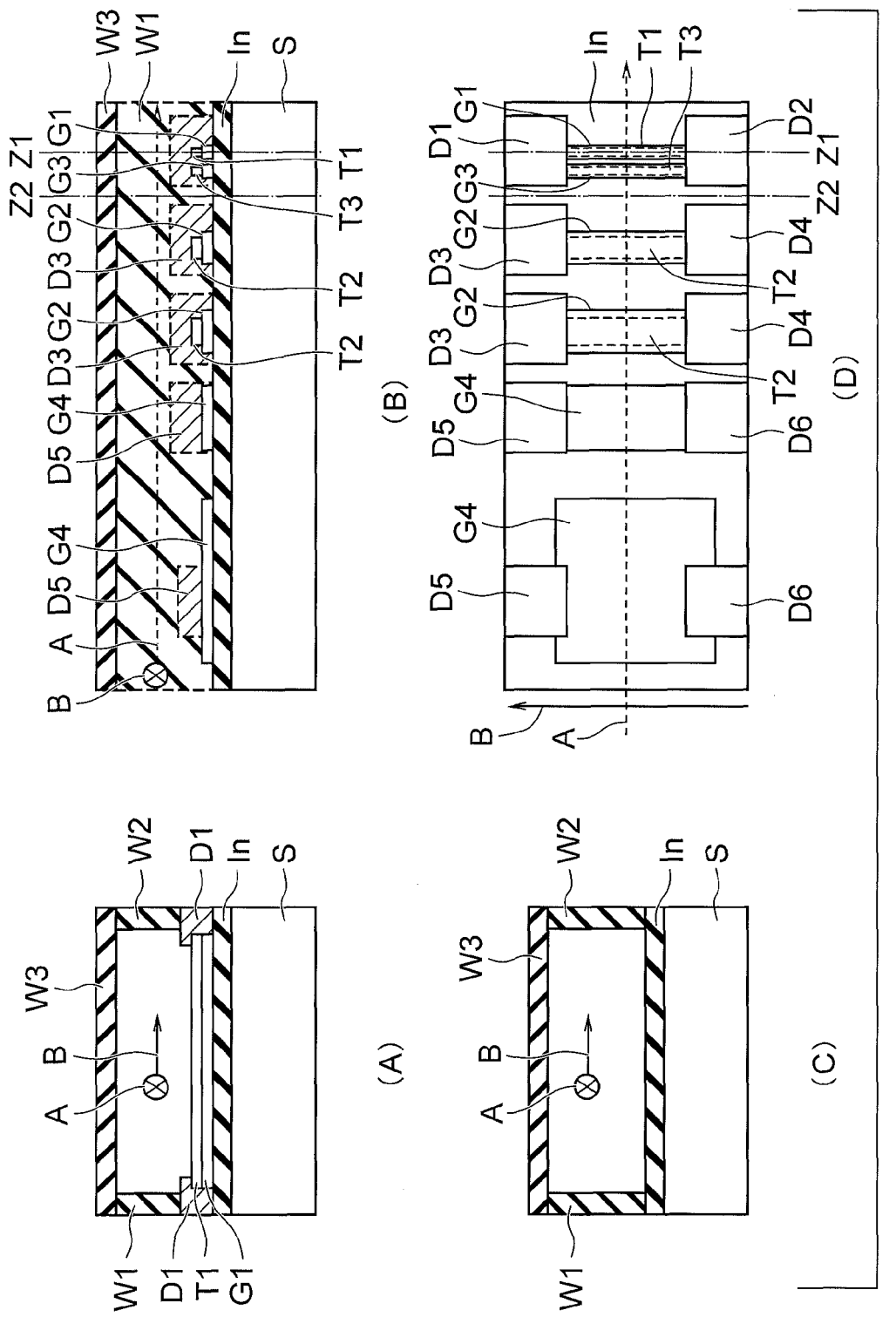
FIG. 15 is a diagram showing a configuration of a biosensor according to a third embodiment.

FIG. 15 is a diagram showing a configuration of a biosensor according to a third embodiment. (A) of FIG. 15 is a cross-sectional view of the biosensor taken along the plane "Z1" perpendicular to the first direction "A" of the flow path of the detection target substance of the biosensor. (B) of FIG. 15 is a cross-sectional view of the biosensor taken along the first direction "A" of the flow path of the detection target substance of the biosensor. (C) of FIG. 15 is a cross-sectional view of the biosensor taken along the plane "Z2" perpendicular to the first direction "A" of the flow path of the detection target substance of the biosensor. (D) of FIG. 15 is a top view of the biosensor. In (D) of FIG. 15, illustration of the first side wall insulating layer "W1", the second side wall insulating layer "W2" and the upper insulating layer "W3" is omitted. In FIG. 15, the same reference symbols as those in FIG. 5 denote the same components as those in the first embodiment, and description of the components will be omitted.

As shown in FIG. 15, the biosensor includes the substrate "S", the insulating layer "In", the first graphene film "G1", the second graphene film "G2", the third graphene film "G3", the fourth graphene film "G4", the first electrode "D1", the second electrode "D2", the third electrode "D3", the fourth electrode "D4", the fifth electrode "D5", the sixth electrode "D6", the first side wall insulating layer "W1", the second wide wall insulating layer "W2", the upper insulating layer "W3", and protective films "T1", "T2", and "T3", for example.

That is, the biosensor according to this embodiment differs from the biosensor according to the first embodiment in that the biosensor further includes the protective films "T1", "T2" and "T3".

The protective film "T1" is provided on the first graphene film "G1" in such a manner that the edge of the first graphene film "G1" that is parallel with the second direction "B" and the edge of the first graphene film "G1" that is opposed to the edge that is parallel with the second direction "B" are exposed.

The protective film "T1" prevents the detection target substance or the liquid containing the detection target substance from coming into contact with the part of the surface of the first graphene film "G1" that is covered with the protective film "T1".

As a result, the bulk conduction-induced characteristics of the first graphene film "G1" can be reduced, and the edge state-induced characteristics can be made more detectable.

The protective film "T2" is provided on the second graphene film "G2" in such a manner that the edge of the second graphene film "G2" that is parallel with the second direction "B" and the edge of the second graphene film "G2" that is opposed to the edge that is parallel with the second direction "B" are exposed.

The protective film "T2" prevents the detection target substance or the liquid containing the detection target substance from coming into contact with the part of the surface of the second graphene film "G2" that is covered with the protective film "T2".

As a result, the bulk conduction-induced characteristics of the second graphene film "G2" can be reduced, and the edge state-induced characteristics can be made more detectable.

The protective film "T3" is provided on the third graphene film "G3" in such a manner that the edge of the third graphene film "G3" that is parallel with the second direction "B" and the edge of the third graphene film "G3" that is opposed to the edge that is parallel with the second direction "B" are exposed.

The protective film "T3" prevents the detection target substance or the liquid containing the detection target substance from coming into contact with the part of the surface of the third graphene film "G3" that is covered with the protective film "T3".

As a result, the bulk conduction-induced characteristics of the third graphene film "G3" can be reduced, and the edge state-induced characteristics can be made more detectable.

No protective film is provided on the fourth graphene film "G4".

Therefore, for the fourth graphene film "G4", the bulk conduction-induced characteristics is detected along with the edge state-induced characteristics.

A method of manufacturing the biosensor according to this embodiment differs from the method of manufacturing the biosensor according to the first embodiment in that, following the step shown in FIG. 8 according to the first embodiment, the method further includes steps of forming the protective films "T1" to "T3" on the first to third graphene films "G1" to "G3" in such a manner that the edges of the first to third graphene films "G1" to "G3" that are parallel with the second direction "B" and the edges of the first to third graphene films "G1" to "G3" that are opposed to the edges that are parallel with the second direction "B" are exposed.

In other respects, the configuration of the biosensor shown in FIG. 15 and the method of manufacturing the biosensor are the same as those of the biosensor shown in FIG. 5.

The remainder of the characteristics of the operation of the biosensor is the same as that in the first embodiment.

That is, the biosensor according to this embodiment can detect a detection target substance with high sensitivity.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A sensor that detects a detection target substance, comprising: an insulating layer; a first graphene film that is provided on the insulating layer so as to be located in a flow path of a liquid containing the detection target substance, the first graphene film having a first edge that is parallel with a first direction that is along the flow path and a second edge that is parallel with a second direction that is different from the first direction, and the first graphene film having the shape of a band that extends in the second direction; a first electrode that is electrically connected to the first edge of the first graphene film that is parallel with the first direction; and a second electrode that is electrically connected to a third edge of the first graphene film that is opposed to the first edge that is parallel with the first direction.

2. The sensor according to claim 1, wherein a width of the first graphene film in the first direction is equal to or smaller than a first prescribed value previously set, and the first prescribed value is 100 nm.

3. The sensor according to claim 1, wherein the second edge of the first graphene film that is parallel with the second direction and a fourth edge of the first graphene film that is opposed to the second edge that is parallel with the second direction are zigzag edges.

4. The sensor according to claim 1, wherein the second edge of the first graphene film that is parallel with the second direction and a fourth edge of the first graphene film that is opposed to the second edge that is parallel with the second direction are armchair edges.

5. The sensor according to claim 1,
wherein the insulating layer is provided on a substrate, and
wherein the first direction and the second direction are perpendicular to each other in a plane that is parallel with an upper surface of the substrate.

6. The sensor according to claim 1, further comprising:
a protective film that is provided on the first graphene film in such a manner that the second edge of the first graphene film that is parallel with the second direction and a fourth edge that is opposed to the second edge that is parallel with the second direction are exposed,
wherein the protective film prevents the liquid containing the detection target substance from coming into contact with a part of a surface of the first graphene film that is covered with the protective film.

7. The sensor according to claim 2, further comprising:
a second graphene film that is provided on the insulating layer so as to be located in the flow path and has the shape of a band that extends in the second direction; a third electrode that is electrically connected to a first edge of the second graphene film that is parallel with the first direction; and a fourth electrode that is electrically connected to a second edge of the second graphene film that is opposed to the first edge that is parallel with the first direction, wherein a width of the second graphene film in the first direction is equal to or smaller than the first prescribed value and is different from the width of the first graphene film in the first direction.

8. The sensor according to claim 7, further comprising:
a third graphene film that is provided on the insulating layer so as to be located in the flow path and has the shape of a band that extends in the second direction,
wherein: a width of the third graphene film in the first direction is equal to or smaller than the first prescribed value, the first electrode is electrically connected to a first edge of the third graphene film that is parallel with the first direction, and the second electrode is electrically connected to a second edge of the third graphene film that is opposed to the first edge that is parallel with the first direction.

9. The sensor according to claim 8, further comprising:
a fourth graphene film that is provided on the insulating layer so as to be located in the flow path and has the shape of a band that extends in the second direction;
a fifth electrode that is electrically connected to a first edge of the fourth graphene film that is parallel with the first direction; and a sixth electrode that is electrically connected to a second edge of the fourth graphene film that is opposed to the first edge that is parallel with the first direction, wherein a width of the fourth graphene film in the first direction is equal to or greater than a second prescribed value that is greater than the first prescribed value.

10. The sensor according to claim 9, wherein the second prescribed value is equal to or greater than 1 μm.

11. The sensor according to claim 1, wherein the first electrode and the second electrode contain any of Al, Cu, W and Ni.

12. The sensor according to claim 1, wherein the insulating layer is a silicon oxide film.

13. The sensor according to claim 1, wherein:
the first electrode is provided on the insulating layer and the first edge of the first graphene film that is parallel with the first direction, and the second electrode is provided on the insulating layer and the third edge of the first graphene film that is opposed to the first edge that is parallel with the first direction.

14. The sensor according to claim 1, further comprising:
a first side wall insulating layer that is provided on the insulating layer along the first direction on a right side of the flow path; a second side wall insulating layer that is provided on the insulating layer along the first direction on a left side of the flow path; and an upper insulating layer that is provided above the flow path along the first direction and is connected to upper parts of the first and second side wall insulating layers.

15. A method of manufacturing a sensor that detects a detection target substance, comprising: forming an insulating layer on a substrate; forming a first graphene film on the insulating layer so as to be located in a flow path of a liquid containing the detection target substance, the first graphene film having a first edge that is parallel with a first direction that is along the flow path and a second edge that is parallel with a second direction that is different from the first direction, and the first graphene film having the shape of a band that extends in the second direction; and forming a first electrode that is electrically connected to the first edge of the first graphene film that is parallel with the first direction and a second electrode that is electrically connected to a third edge of the first graphene film that is opposed to the first edge that is parallel with the first direction.

16. The method of manufacturing a sensor according to claim 15, wherein a width of the first graphene film in the first direction is equal to or smaller than a first prescribed value previously set, and the first prescribed value is 100 nm.

17. The method of manufacturing a sensor according to claim 15, further comprising:
forming a protective film on the first graphene film in such a manner that the second edge of the first graphene film that is parallel with the second direction and a fourth edge that is opposed to the second edge that is parallel with the second direction are exposed.

18. The method of manufacturing a sensor according to claim 16, further comprising:
forming a second graphene film on the insulating layer so as to be located in the flow path, the second graphene film having the shape of a band that extends in the second direction; forming a third electrode that is electrically connected to a first edge of the second graphene film that is parallel with the first direction and a fourth electrode that is electrically connected to a second edge of the second graphene film that is opposed to the first edge that is parallel with the first direction, wherein a width of the second graphene film in the first direction is equal to or smaller than the first prescribed value and is different from the width of the first graphene film in the first direction.

19. The method of manufacturing a sensor according to claim 15, further comprising:
forming a first side wall insulating layer on the insulating layer along the first direction on a right side of the flow path, a second side wall insulating layer on the insulating layer along the first direction on a left side of the flow path, and an upper insulating layer that is provided above the flow path along the first direction and is connected to upper parts of the first and second side wall insulating layers.

20. The method of manufacturing a sensor according to claim 15, wherein the first direction and the second direction are perpendicular to each other in a plane that is parallel with an upper surface of the substrate.

\* \* \* \* \*